(12) United States Patent
Hirata

(10) Patent No.: US 8,138,370 B2
(45) Date of Patent: Mar. 20, 2012

(54) METHOD OF PRODUCING OPTICALLY ACTIVE α-AMINO ACID BENZYL ESTERS

(75) Inventor: Norihiko Hirata, Suita (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 214 days.

(21) Appl. No.: 12/440,479

(22) PCT Filed: Aug. 20, 2007

(86) PCT No.: PCT/JP2007/066497
§ 371 (c)(1),
(2), (4) Date: Mar. 10, 2009

(87) PCT Pub. No.: WO2008/032546
PCT Pub. Date: Mar. 20, 2008

(65) Prior Publication Data
US 2010/0010254 A1    Jan. 14, 2010

(30) Foreign Application Priority Data
Sep. 12, 2006 (JP) ................................. 2006-246418

(51) Int. Cl.
*C07C 229/00* (2006.01)
(52) U.S. Cl. ............................................. 560/173
(58) Field of Classification Search .............. None
See application file for complete search history.

(56) References Cited

U.S. PATENT DOCUMENTS
| | | |
|---|---|---|
| 6,706,916 B1 | 3/2004 | Sato et al. |
| 2004/0133033 A1 | 7/2004 | Vitrant et al. |

FOREIGN PATENT DOCUMENTS
| | | |
|---|---|---|
| EP | 0309324 A1 | 3/1989 |
| EP | 0985658 A1 | 3/2000 |
| EP | 1156032 A1 | 11/2001 |
| EP | 1439166 A1 | 7/2004 |
| JP | 7206792 A | 8/1995 |
| JP | 11263757 A | 9/1999 |
| JP | 2000-247934 A | 9/2000 |
| JP | 2000319239 A | 11/2000 |
| JP | 2004203874 A | 7/2004 |
| WO | 9947488 A1 | 9/1999 |

OTHER PUBLICATIONS

Aldrich, Aldrich Handbook of Fine Chemicals and Laboratory Equipment, 2002, Milwaukee, WI, pp. 359 and 823.*
Leonidas Zervas, et al., "Studies on Arginine Peptides. I. Intermediates in the Syntheseis of N-Terminal and C-Terminal Arginine Peptides", J. Org. Chem., pp. 1515-1521, (1957).
Extended EP Search Report issued Mar. 18, 2011 from the European Patent Office in counterpart EP Application No. 07 792 979.2.
Winitz et al.: "Studies on Diastereoisomeric alpha-Amino Acids and Corresponding alpha-Hydroxy Acids. VII. Influence of beta-Configuration and Enzymic Susceptibility"; Journal of the American Chemical Society; (78); pp. 2423-2430 (1956).
Miller et al: "Benzyl Esters of Amino Acids"; Journal of American Chemical Society; (74); pp. 1092-1093 (1952).
von Eugen Schnabel: "L-Seryl-Glycyl-L-Alanyl-Glycl-L-Alanyl-Glycyl-L-Tyrosin"; Justus Liebigs Annalen der Chemie; pp. 181-187 (1959).
Hashimoto et al: Studies of Poly-beta-benzyl-L-aspartate Helix. I. The Synthesis and Rotatory Dispersion of Copolymers of beta-p-Methyl, Chloro, Cyano, or Nitrobenzyl-L-aspartate with beta-Benzyl-L-aspartate; Bulletin of the Chemical Society of Japan; (39); pp. 2707-2713 (1966).

* cited by examiner

*Primary Examiner* — Paul A Zucker
(74) *Attorney, Agent, or Firm* — Panitch Schwarze Belisario & Nadel LLP

(57) ABSTRACT

A method is provided for producing optically active α-amino acid benzyl esters. The method includes reacting an optically active α-amino acid and benzyl alcohols in the presence of an acid, wherein the reaction is carried out under reduced pressure without substantially using a solvent, while distilling off water generated by the progress of the reaction.

11 Claims, No Drawings

METHOD OF PRODUCING OPTICALLY ACTIVE α-AMINO ACID BENZYL ESTERS

CROSS-REFERENCE TO RELATED APPLICATION

This application is a section 371 of International Application No. PCT/JP2007/066497, filed Aug. 20, 2007, which was published in the Japanese language on Mar. 20, 2008 under International Publication No. WO 2008/032546 A1 and the disclosure of which is incorporated herein by reference.

TECHNICAL FIELD

The present invention relates to a method of producing optically active α-amino acid benzyl esters.

BACKGROUND ART

Optically active α-amino acid benzyl esters are compounds useful as chemical raw materials or medical agricultural chemical intermediates, and as the production method thereof, there is known a method in which an optically active α-amino acid and benzyl alcohols are reacted in the presence of an organic solvent and an acid under normal pressure condition, while dehydrating azeotropically (see, for example, non-patent document 1). This method, however, has a problem that α-amino acid benzyl esters of high optical purity cannot be obtained since also racemization progresses together with the esterification. For solving such a problem, a method has been developed in which the above-described reaction is carried out in the absence of oxygen or in the presence of hydrazines (see, for example, patent document 1), however, this method is not industrially satisfactory in the aspect of yield.
[patent document 1] JP-A No. 2000-247934
[non-patent document 1] J. Org. Chem., 22, 1515 (1957)

DISCLOSURE OF THE INVENTION

The present inventors have investigated a method for producing optically active α-amino acid benzyl esters with good yield, and resultantly found that the targeted esterification reaction progresses with good yield while suppressing progress of racemization, by carrying out the above-described reaction under reduced pressure without substantially using a solvent, while distilling off water generated by the progress of the reaction.

That is, the present invention provides the following [1] to [12].

[1]. A method of producing optically active α-amino acid benzyl esters comprising reacting an optically active α-amino acid and benzyl alcohols of the formula (1):

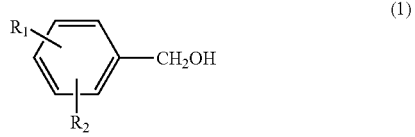

(1)

(wherein, $R^1$ and $R^2$ are mutually the same or different and represent a hydrogen atom, alkyl group having 1 to 6 carbon atoms, alkoxy group having 1 to 6 carbon atoms, nitro group, cyano group or halogen atom.)

in the presence of an acid, wherein the reaction is carried out under reduced pressure without substantially using a solvent, while distilling off water generated by the progress of the reaction.

[2]. The production method according to [1], wherein the acid is an organic sulfonic acid.

[3]. The production method according to [1], wherein the acid is p-toluene sulfonic acid.

[4]. The production method according to any one of [1] to [3], wherein the use amount of the acid is within a range of the sum of 1 mole ratio with respect to an amino group of the optically active α-amino acid and 0.05 to 0.2 mole ratio with respect to a carboxyl group of the optically active α-amino acid.

[5]. The production method according to any one of [1] to [4], wherein the reaction temperature is within a range of 40 to 70° C.

[6]. The production method according to any one of [1] to [5], wherein the pressure in the reaction is within a range of 0.5 to 2 kPa.

[7]. The production method according to any one of [1] to [6], wherein optically active α-amino acid benzyl esters are collected in the form of salt, by performing a crystallization treatment of the reaction mixture using an organic solvent.

[8]. The production method according to [7], wherein the pressure in the crystallization treatment is normal pressure.

[9]. The production method according to [7] or [8], wherein the organic solvent is an ether solvent.

[10]. The production method according to [9], wherein the ether solvent is tert-butyl methyl ether.

[11]. The production method according to any one of [1] to [10], wherein the optically active α-amino acid is L-alanine.

[12]. The production method according to any one of [1] to [11], wherein $R^1$ and $R^2$ in the formula (1) both represent a hydrogen atom.

MODES FOR CARRYING OUT THE INVENTION

The present invention will be described in detail below.

The optically active α-amino acid to be used in the present invention denotes an optically active organic compound having an amino group (—$NH_2$) and a carboxyl group (—COOH) on the same carbon atom, in which the carbon atom is asymmetric center.

Examples of the optically active α-amino acid include optically active alanine, optically active phenylalanine, optically active valine, optically active isoleucine, optically active leucine, optically active aspartic acid, optically active glutamic acid, optically active histidine, optically active lysine, optically active proline and the like, and any of L bodies and D bodies may be used, and also a mixture of L bodies and D bodies may be used. As these compounds, those naturally existing may be used, and those synthesized by any known methods may also be used.

In the benzyl alcohols of the formula (1) (hereinafter, abbreviated as benzyl alcohols (1)), examples of the alkyl group having 1 to 6 carbon atoms represented by $R^1$ and $R^2$ include a methyl group, ethyl group, propyl group, isopropyl group, butyl group, tert-butyl group, pentyl group, hexyl group and the like, examples of the alkoxy group having 1 to 6 carbon atoms include a methoxy group, ethoxy group, propoxy group, isopropoxy group, butoxy group, tert-butoxy group, pentyloxy group, hexyloxy group and the like, and the halogen atom includes a fluorine atom, chlorine atom, bromine atom and iodine atom.

Specific examples of the benzyl alcohols (1) include benzyl alcohol, 2-methylbenzyl alcohol, 3-methylbenzyl alcohol, 4-methylbenzyl alcohol, 4-ethylbenzyl alcohol, 4-propylbenzyl alcohol, 4-isopropylbenzyl alcohol, 4-n-butylbenzyl alcohol, 4-tert-butylbenzyl alcohol, 4-pentylbenzyl alcohol, 4-hexylbenzyl alcohol, 2,3-dimethylbenzyl alcohol, 2,4-dimethylbenzyl alcohol, 2,5-dimethylbenzyl alcohol, 3,4-dimethylbenzyl alcohol, 3,5-dimethylbenzyl alcohol, 2-methoxybenzyl alcohol, 3-methoxybenzyl alcohol, 4-methoxybenzyl alcohol, 4-ethoxybenzyl alcohol, 4-propoxybenzyl alcohol, 4-isopropoxybenzyl alcohol, 4-n-butoxybenzyl alcohol, 4-tert-butoxybenzyl alcohol, 4-pentyloxybenzyl alcohol, 4-hexyloxybenzyl alcohol, 2,3-dimethoxybenzyl alcohol, 2,4-dimethoxybenzyl alcohol, 2,5-dimethoxybenzyl alcohol, 3,4-dimethoxybenzyl alcohol, 3,5-dimethoxybenzyl alcohol, 4-nitrobenzyl alcohol, 4-cyanobenzyl alcohol, 4-fluorooxybenzyl alcohol, 4-chlorobenzyl alcohol and the like. As these compounds, those commercially available can be used, and for example, those synthesized by known methods such as subjecting corresponding benzoic acids to a reducing reaction, and the like, can also be used.

The use amount of the benzyl alcohols (1) may advantageously be 1 equivalent or more with respect to a carboxy group of the optically active α-amino acid, and its upper limit is not restricted, however, when economical aspect is taken into consideration, it is usually 1 to 10 equivalents, preferably 1.1 to 7 equivalents. Specifically, in the case, for example, of alanine having one carboxy group, the use amount of the benzyl alcohols (1) is usually 1 to 10 mol, preferably 1.1 to 7 mol with respect to 1 mol of alanine. For example, in the case of aspartic acid having two carboxy groups, the use amount of the benzyl alcohols (1) is usually 2 to 20 mol, preferably 2.2 to 14 mol with respect to 1 mol of aspartic acid.

As the acid, for example, mineral acids such as sulfuric acid, hydrochloric acid and the like can be used, however, organic sulfonic acids such as methanesulfonic acid, p-toluenesulfonic acid and the like are usually used. p-toluenesulfonic acid is preferable. These acids may be used in any form of hydrate, anhydride and solution.

The use amount of the acid is 1 mole ratio with respect to an amino group of an optically active α-amino acid for neutralization of the amino group, and in addition, usually 0.01 to 1 mole ratio, preferably 0.05 to 0.2 mole ratio with respect to a carboxyl group of an optically active α-amino acid. Specifically, in the case, for example, of alanine having one amino group and one carboxy group, the use amount of the acid is usually 1.01 to 2 mole ratio, preferably 1.05 to 1.2 mole ratio with respect to 1 mol of alanine. For example, in the case of aspartic acid having one amino group and two carboxy groups, the use amount of the acid is usually 1.02 to 3 mole ratio, preferably 1.1 to 1.4 mole ratio with respect to 1 mol of aspartic acid.

The pressure in the reaction is usually 0.1 to 50 kPa, preferably 0.5 to 2 kPa. The reaction temperature is usually 20 to 100° C., preferably 40 to 70° C. It is preferable to carry out the reaction under pressure condition of 0.5 to 2 kPa and in a range of 40 to 70° C.

The operation order of the reaction is not particularly restricted, and for example, an optically active α-amino acid, benzyl alcohols (1) and acid are mixed in any order under normal pressure, a given pressure is adjusted, then, the temperature is raised gradually, thereby, water generated by the progress of the reaction is distilled off, to prevent reflux flow of water into the reaction system. Here, if those containing water are used as the optically active α-amino acid, benzyl alcohols (1) or acid, it may be permissible that water contained in them are distilled off together with water generated by the progress of the reaction.

The progress of the reaction can be confirmed by usual analysis means such as, for example, gas chromatography, high performance liquid chromatography, thin layer chromatography, nuclear magnetic resonance spectrum analysis, infrared absorption spectrum analysis and the like.

Examples of the optically active α-amino acid benzyl esters obtained by this reaction include optically active alanine benzyl ester, optically active phenylalanine benzyl ester, optically active valine benzyl ester, optically active isoleucine benzyl ester, optically active leucine benzyl ester, optically active aspartic acid benzyl ester, optically active glutamic acid benzyl ester, optically active histidine benzyl ester, optically active lysine benzyl ester, optically active proline benzyl ester, and compounds obtained by substituting benzyl ester parts of the above-described compounds by 2-methyl benzyl ester, 3-methyl benzyl ester, 4-methyl benzyl ester, 4-ethyl benzyl ester, 4-propyl benzyl ester, 4-isopropyl benzyl ester, 4-n-butyl benzyl ester, 4-tert-butyl benzyl ester, 4-pentyl benzyl ester, 4-hexyl benzyl ester, 2,3-dimethyl benzyl ester, 2,4-dimethyl benzyl ester, 2,5-dimethyl benzyl ester, 3,4-dimethyl benzyl ester, 3,5-dimethyl benzyl ester, 2-methoxy benzyl ester, 3-methoxy benzyl ester, 4-methoxy benzyl ester, 4-ethoxy benzyl ester, 4-propoxy benzyl ester, 4-isopropoxy benzyl ester, 4-n-butoxy benzyl ester, 4-tert-butoxy benzyl ester, 4-pentyloxy benzyl ester, 4-hexyloxy benzyl ester, 2,3-dimethoxy benzyl ester, 2,4-dimethoxy benzyl ester, 2,5-dimethoxy benzyl ester, 3,4-dimethoxy benzyl ester, 3,5-dimethoxy benzyl ester, 4-nitro benzyl ester, 4-cyano benzyl ester, 4-fluorooxy benzyl ester or 4-chlorobenzyl ester, respectively, and the like. The optical purity of these optically active α-amino acid benzyl esters keeps substantially the optical purity of the optically active α-amino acid used as a raw material.

After completion of the reaction, for example, the reaction mixture may be neutralized using a base such as sodium hydroxide and the like and optically active α-amino acid benzyl esters may be removed, however, such compounds are usually unstable and removal thereof with good purity is difficult, thus, it is preferable to collect the optically active α-amino acid benzyl esters in the form of salt by performing a crystallization treatment of the reaction mixture using an organic solvent.

Examples of the organic solvent include aliphatic hydrocarbon solvents such as hexane, heptane and the like; ether solvents such as diethyl ether, tert-butyl methyl ether and the like; aromatic hydrocarbon solvents such as toluene, xylene, benzene and the like; ester solvents such as methyl acetate, ethyl acetate and the like; and so on. Ether solvents are preferable, and tert-butyl methyl ether is more preferable. The use amount of the organic solvent is usually 5 to 60 weight ratio, preferably 20 to 40 weight ratio with respect to the optically active α-amino acid.

The crystallization treatment is carried out usually by returning the pressure to normal pressure, then, mixing the reaction mixture and an organic solvent, and the mixing order thereof is not particularly restricted. The temperature in the crystallization treatment is usually −50 to 80° C., preferably −10 to 60° C. When a crystal deposits immediately by mixing the reaction mixture and an organic solvent, a solid-liquid separation treatment described later may be carried out as it is, or a solid-liquid separation treatment may be carried out after further cooling in the above-described temperature range. When a crystal does not deposit in the time point of mixing of the reaction mixture and an organic solvent, it may be advantageous to carry out a solid-liquid separation treatment after causing deposition of a crystal by cooling in the above-described temperature range. In this case, a salt of optically active α-amino acid benzyl esters may be used as a seed crystal. The seed crystal may be added after mixing of the reaction mixture and an organic solvent, or may be added during the mixing.

In a more preferable embodiment of the crystallization treatment, an organic solvent is added to the reaction mixture in a range of 30 to 60° C., and during this procedure, the above-described seed crystal is added, then, an organic solvent is further added, then, the resultant mixture is cooled down to a range of −10 to 20° C.

After completion of the crystallization treatment, a salt of optically active α-amino acid benzyl esters can be collected as solid from the resultant mixture, by a usual solid-liquid separation treatment such as a filtration treatment and the like. The resultant solid may be further subjected to a washing treatment. As the solvent used in the washing treatment, organic solvents used in the crystallization treatment are mentioned.

As the salt of optically active α-amino acid benzyl esters thus obtained, salts of the above-described optically active α-amino acid benzyl esters and the above-described acids are mentioned.

According to the present invention, α-amino acid benzyl esters of high optical purity can be produced with good yield, giving industrial advantage.

When the reaction mixture is subjected as it is to the crystallization treatment using an organic solvent (preferably, ether solvent), optically active α-amino acid benzyl esters as unstable compounds can be taken out in the form of stable salt efficiently.

EXAMPLES

The present invention will be illustrated further in detail referring to examples below, but it is needless to say that the present invention is not restricted by these examples.

Example 1

Into a 300 mL separable flask equipped with a thermometer, stirring apparatus and Dean Stark apparatus was charged 5.00 g (56.12 mmol) of L-alanine, 41.03 g (379.42 mmol) of benzyl alcohol and 12.81 g (67.34 mmol) of p-toluenesulfonic acid, and mixed, then, the pressure was reduced from 101.3 kPa to 2.0 kPa. The reaction solution was heated, then, water started to be distilled at the inner temperature around 50° C., and the mixture was heated up to 62° C. over a period of 2 hours. Under the same pressure and the same temperature, the mixture was stirred for 3.5 hours. The reaction solution was cooled down to 50° C., and 111.66 g of tert-butyl methyl ether was dropped over a period of 30 minutes, then, about 0.005 g (0.01 mmol) of p-toluenesulfonate of L-alanine benzyl ester was added. The mixture was stirred at 50° C. for 30 minutes, then, 55.83 g of tert-butyl methyl ether was dropped over a period of 1 hour. The mixture was stirred at 50° C. for 1 hour, then, cooled from 50° C. to 0° C. over a period of 5 hours, and the mixture was stirred at 0° C. overnight. The mixture was subjected to a filtration treatment, and the resultant crystal was washed three times with 15.00 g of tert-butyl methyl ether of 0° C. After drying, 18.26 g of p-toluenesulfonate of L-alanine benzyl ester was obtained. The yield against L-alanine was 98.6%. The optical purity of the p-toluenesulfonate of L-alanine benzyl ester was 99.9% e.e. or more.

The invention claimed is:

1. A method of producing optically active α-amino acid benzyl esters comprising reacting an optically active α-amino acid and benzyl alcohols of the formula (1):

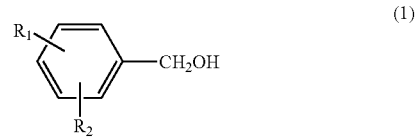

wherein $R^1$ and $R^2$ are mutually the same or different and represent a hydrogen atom, alkyl group having 1 to 6 carbon atoms, alkoxy group having 1 to 6 carbon atoms, nitro group, cyano group or halogen atom in the presence of an acid, wherein the reaction is carried out at a reaction temperature within a of 40 to 70° C. under reduced pressure without using a solvent, while distilling off water generated by the progress of the reaction.

2. The production method according to claim 1, wherein the acid is an organic sulfonic acid.

3. The production method according to claim 1, wherein the acid is p-toluene sulfonic acid.

4. The production method according to claim 1, wherein the acid is provided in an amount calculated as a sum of a molar amount of an amino group in the optically active α-amino acid plus 0.05 to 0.2 times a molar amount of a carboxyl group in the optically active α-amino acid.

5. The production method according to claim 1, wherein the pressure in the reaction is within a range of 0.5 to 2 kPa.

6. The production method according to claim 1, wherein optically active α-amino acid benzyl esters are collected in the form of salt, by performing a crystallization treatment of the reaction mixture using an organic solvent.

7. The production method according to claim 6, wherein the pressure in the crystallization treatment is normal pressure.

8. The production method according to claim 6, wherein the organic solvent is an ether solvent.

9. The production method according to claim 8, wherein the ether solvent is tert-butyl methyl ether.

10. The production method according to claim 1, wherein the optically active α-amino acid is L-alanine.

11. The production method according to claim 1, wherein $R^1$ and $R^2$ in the formula (1) both represent a hydrogen atom.

* * * * *